US012412270B2

United States Patent
Mazumder et al.

(10) Patent No.: US 12,412,270 B2
(45) Date of Patent: Sep. 9, 2025

(54) METHOD AND SYSTEM FOR DETERMINING PROGRESSION OF ATRIAL FIBRILLATION BASED ON HEMODYNAMIC METRICS

(71) Applicant: Tata Consultancy Services Limited, Mumbai (IN)

(72) Inventors: Oishee Mazumder, Kolkata (IN); Aniruddha Sinha, Kolkata (IN); Dibyendu Roy, Kolkata (IN); Shivam Gupta, Gwalior (IN)

(73) Assignee: Tata Consultancy Services Limited, Mumbai (IN)

( * ) Notice: Subject to any disclaimer, the term of this patent is extended or adjusted under 35 U.S.C. 154(b) by 306 days.

(21) Appl. No.: 18/347,810

(22) Filed: Jul. 6, 2023

(65) Prior Publication Data

US 2024/0013382 A1    Jan. 11, 2024

(30) Foreign Application Priority Data

Jul. 10, 2022    (IN) .............................. 202221039572

(51) Int. Cl.
*G06T 7/00*    (2017.01)

(52) U.S. Cl.
CPC .. *G06T 7/0012* (2013.01); *G06T 2207/10081* (2013.01); *G06T 2207/10088* (2013.01); *G06T 2207/30048* (2013.01)

(58) Field of Classification Search
None
See application file for complete search history.

(56) References Cited

U.S. PATENT DOCUMENTS 10,052,158 B2    8/2018   Taylor
2019/0183579 A1   6/2019   Kosior et al.

OTHER PUBLICATIONS

Duenas-Pamplona Jorge etal: "A Comprehensive Comparison of Various Patient-Specific CFD Models Of The Left Atrium For Atrial Fibrillation Patients", Computers in Biology and Medicine, New York, NY, US, vol. 133, Apr. 24, 2021 (Apr. 24, 2021) (Year: 2021).*

(Continued)

*Primary Examiner* — Twyler L Haskins
(74) *Attorney, Agent, or Firm* — Finnegan, Henderson, Farabow, Garrett & Dunner, LLP

(57) ABSTRACT

The present invention relates to a method and system for determining progression of atrial fibrillation (AF) based on hemodynamic metrics. In conventional CFD models, effect of the AF on a cardiovascular system is not modeled and evaluation of associated hemodynamic metrics and its effect on a Left Atrium (LA) dynamics is not considered. The method and system for determining progression of the AF based on the hemodynamic metrics, analyzes the effect of the AF on cardiovascular parameters of the LA and a left Ventricle (LV), for AF variations. A 3D-CFD model is modelled from a plurality of scan images of a heart of a subject and the AF variations are incorporated in a zero-dimensional (0D) lumped cardiovascular hemodynamic model along with a novel rhythm generator that are used for extracting a plurality of LA hemodynamic metrics of wall shear stress (WSS) that are possible indicators for progression of the AF.

18 Claims, 8 Drawing Sheets

(56) References Cited

OTHER PUBLICATIONS

Alberto Zingaro et al: "A multiscale CFO model of blood flow in the human left heart coupled with a lumped-parameter model of the cardiovascular system", arxiv.org, Cornell University Library, 201 Olin Library Cornell University Ithaca, NY 14853, Oct. 5, 2021 (Year: 2021).*

Mattia Corti et al: "Impact of Atrial Fibrillation on Left Atrium Haemodynamics: A Computational Fluid Dynamics Study", arxiv. org, Cornell University Library, 201 Olin Library Cornell University Ithaca, NY 14853, Feb. 22, 2022 (Feb. 22, 2022) (Year: 2022).*

Alessandro Masci et al. "Development of a Computational Fluid Dynamics Model of the Left Atrium in Atrial Fibrillation on a Patient Specific Basis," Computing in Cardiology, 2017, vol. 44, https://www.cinc.org/archives/2017/pdf/004-429.pdf.

Roberto Piersanti et al. "3D-0D closed-loop model for the simulation of cardiac biventricular electromechanics," Computer Methods in Applied Mechanics and Engineering, Mar. 2022, vol. 391, Elsevier, https://www.sciencedirect.com/science/article/pii/S0045782522000251.

Sethuraman Sankaran et al. "Patient-specific multiscale modeling of blood flow for coronary artery bypass graft surgery," Ann Biomed Eng, Oct. 2012, Biomedical Engineering Society Link: https://www.ncbi.nlm.nih.gov/pmc/articles/PMC3570226/pdf/nihms436305.pdf.

Mattia Corti et al. "Impact of Atrial Fibrillation on Left Atrium Haemodynamics: A Computational Fluid Dynamics Study," Computers in Biology and Medicine, Nov. 2022, Elsevier, https://arxiv.org/abs/2202.10893.

* cited by examiner

METHOD AND SYSTEM FOR DETERMINING PROGRESSION OF ATRIAL FIBRILLATION BASED ON HEMODYNAMIC METRICS

PRIORITY CLAIM

This U.S. patent application claims priority under 35 U.S.C. § 119 to: Indian provisional patent application No. 202221039572, filed on Jul. 10, 2022. The entire contents of the aforementioned application are incorporated herein by reference.

TECHNICAL FIELD

The disclosure herein generally relates to the field of health monitoring, and, more particularly, to a method and system for determining progression of atrial fibrillation (AF) based on hemodynamic metrics.

BACKGROUND

Atrial fibrillation (AF) is a form of cardiac arrhythmia causing rapid and disorganized beating of an atrium. The AF is mostly triggered by electrical impulses originating in roots of pulmonary veins in a left atrium (LA), and effects the LA functionality in general. Prevalence of the AF is predominantly increasing in older population and though the AF in isolation is not life threatening, it is often accompanied with or can autonomously cause other cardiovascular diseases. The most significant effect associated with the AF is thromboembolism due to a blood stasis inside the LA. Such thromboembolic events are generally precursor to vascular dementia, stroke and infraction leading to heart failure. Hence understanding disease etiology and its manifestation is crucial to predict the thromboembolic event and aid in early diagnosis and management of the AF.

Conventionally the AF is detected mainly through electrocardiogram (ECG). However, several clinical studies suggests that hemodynamic analysis on the LA and a left atrial appendage (LAA) are crucial for risk stratification of the thromboembolic events. A Computational fluid dynamics (CFD) model is a potent tool that could evaluate subject specific structural changes associated with the LA remodeling and link with the hemodynamic analysis and predict chances of the thromboembolic events.

Conventionally the CFD models of the AF have mostly concentrated on an image segmentation pipeline to recreate the related atrium geometry and use simple motion model to estimate cardiac rhythm (pulsatile behavior) of a heart of a subject and computed wall shear stress related variables. However, the effect of the AF on a cardiovascular system has not been modeled. Further some of the conventional CFD models express pressure flow dynamical variation during the AF and its effect on the cardiovascular system through lumped parameter modelling. However, these models do not involve evaluation of associated hemodynamic metrics. Further multiscale conventional approach involving both the CFD, and arterial hemodynamics was implemented to study the flow distribution in aortic circulation due to the AF variations and its relation to stroke but the effect on LA dynamics have not been considered.

SUMMARY

Embodiments of the present disclosure present technological improvements as solutions to one or more of the above-mentioned technical problems recognized by the inventors in conventional systems. For example, in one embodiment, a method for determining progression of atrial fibrillation is provided. The method includes receiving a plurality of medical scan images of a heart of a subject. Further the method includes creating a three-dimensional Computational Fluid Dynamics (3D-CFD) model of a Left Atrium (LA), from the received plurality of medical scan images. Furthermore, the method includes performing discretization on the 3D-CFD model, into a plurality of regions of interest, generating a plurality of high density meshes. Furthermore, the method includes modelling a zero-dimensional (OD) lumped cardiovascular hemodynamic model, to generate a plurality of cardiovascular parameters, wherein the plurality of cardiovascular parameters comprises, a systemic artery flow, a pulmonary artery flow, pressure flow dynamics at the LA (LA dynamics) and pressure flow dynamics at a left ventricle (LV dynamics), a left atrium compliance corresponding to the LA dynamics and, a left ventricle compliance corresponding to the LV dynamics. Upon modelling the zero-dimensional (OD) lumped cardiovascular hemodynamic model, the method performs modelling of an Atrial Fibrillation (AF), by the OD lumped cardiovascular hemodynamic model along with a rhythm generator, to generate cardiac rhythms for a normal sinus rhythm condition and AF conditions, wherein the AF conditions comprises a high frequency AF (HF-AF) rhythm condition and, a LA remodeled AF rhythm condition. Furthermore, the method comprises generating by the OD lumped cardiovascular hemodynamic model, the plurality of cardiovascular parameters, for the LA and the LV, by using the generated cardiac rhythms corresponding to the normal sinus rhythm condition and the AF conditions. Furthermore, the method comprises constructing a plurality of blood inflow boundary conditions at a bilateral pulmonary vein inlets and a plurality of blood outflow boundary conditions at a mitral valve outlet, by using the plurality of cardiovascular parameters of the OD lumped cardiovascular hemodynamic model, generating a boundary conditions imposed 3D-CFD model. Further the method includes calculating a mitral flow blood velocity, on the plurality of high density meshes, by performing a CFD analysis, on the boundary conditions imposed 3D-CFD model. Finally, the method extracts a plurality of LA hemodynamic metrics of wall shear stress (WSS) that are possible indicators for progression of Atrial Fibrillation (AF), from the calculated mitral flow blood velocity, wherein the plurality of LA hemodynamic metrics comprising of time average wall shear stress (TAWSS), oscillatory shear index (OSI) and endothelial cell activation potential (ECAP) are indicators for progression of the AF.

In another aspect, a system for determining progression of atrial fibrillation is provided is provided. The system includes receiving a plurality of medical scan images of a heart of a subject. Further the system includes creating a three-dimensional Computational Fluid Dynamics (3D-CFD) model of a Left Atrium (LA), from the received plurality of medical scan images. Furthermore, the system includes performing discretization on the 3D-CFD model, into a plurality of regions of interest, generating a plurality of high density meshes. Furthermore, the system includes modelling a zero-dimensional (OD) lumped cardiovascular hemodynamic model, to generate a plurality of cardiovascular parameters, wherein the plurality of cardiovascular parameters comprises, a systemic artery flow, a pulmonary artery flow, pressure flow dynamics at the LA (LA dynamics) and pressure flow dynamics at a left ventricle (LV dynamics), a left atrium compliance corresponding to the LA dynamics and, a left ventricle compliance corresponding to the LV dynamics. Upon modelling the zero-dimensional (OD) lumped cardiovascular hemodynamic model, the system performs modelling of an Atrial Fibrillation (AF), by the OD lumped cardiovascular hemodynamic model along with a rhythm generator, to generate cardiac rhythms for a normal sinus rhythm condition and AF conditions, wherein the AF conditions comprises a high frequency AF (HF-AF) rhythm condition and, a LA remodeled AF rhythm condition. Furthermore, the system comprises generating by the OD lumped cardiovascular hemodynamic model, the plurality of cardiovascular parameters, for the LA and the LV, by using the generated cardiac rhythms corresponding to the normal sinus rhythm condition and the AF conditions. Furthermore, the system comprises constructing a plurality of blood inflow boundary conditions at a bilateral pulmonary vein inlets and a plurality of blood outflow boundary conditions at a mitral valve outlet, by using the plurality of cardiovascular parameters of the OD lumped cardiovascular hemodynamic model, generating a boundary conditions imposed 3D-CFD model. Further the system includes calculating a mitral flow blood velocity, on the plurality of high density meshes, by performing a CFD analysis, on the boundary conditions imposed 3D-CFD model. Finally, the system extracts a plurality of LA hemodynamic metrics of wall shear stress (WSS) that are possible indicators for progression of Atrial Fibrillation (AF), from the calculated mitral flow blood velocity, wherein the plurality of LA hemodynamic metrics comprising of time average wall shear stress (TAWSS), oscillatory shear index (OSI) and endothelial cell activation potential (ECAP) are indicators for progression of the AF.

In yet another aspect, there are provided one or more non-transitory machine-readable information storage mediums comprising one or more instructions which when executed by one or more hardware processors cause a method for determining progression of atrial fibrillation. The method includes receiving a plurality of medical scan images of a heart of a subject. Further the method includes creating a three-dimensional Computational Fluid Dynamics (3D-CFD) model of a Left Atrium (LA), from the received plurality of medical scan images. Furthermore, the method includes performing discretization on the 3D-CFD model, into a plurality of regions of interest, generating a plurality of high density meshes. Furthermore, the method includes modelling a zero-dimensional (OD) lumped cardiovascular hemodynamic model, to generate a plurality of cardiovascular parameters, wherein the plurality of cardiovascular parameters comprises, a systemic artery flow, a pulmonary artery flow, pressure flow dynamics at the LA (LA dynamics) and pressure flow dynamics at a left ventricle (LV dynamics), a left atrium compliance corresponding to the LA dynamics and, a left ventricle compliance corresponding to the LV dynamics. Upon modelling the zero-dimensional (OD) lumped cardiovascular hemodynamic model, the method performs modelling of an Atrial Fibrillation (AF), by the OD lumped cardiovascular hemodynamic model along with a rhythm generator, to generate cardiac rhythms for a normal sinus rhythm condition and AF conditions, wherein the AF conditions comprises a high frequency AF (HF-AF) rhythm condition and, a LA remodeled AF rhythm condition. Furthermore, the method comprises generating by the OD lumped cardiovascular hemodynamic model, the plurality of cardiovascular parameters, for the LA and the LV, by using the generated cardiac rhythms corresponding to the normal sinus rhythm condition and the AF conditions. Furthermore, the method comprises constructing a plurality of blood inflow boundary conditions at a bilateral pulmonary vein inlets and a plurality of blood outflow boundary conditions at a mitral valve outlet, by using the plurality of cardiovascular parameters of the OD lumped cardiovascular hemodynamic model, generating a boundary conditions imposed 3D-CFD model. Further the method includes calculating a mitral flow blood velocity, on the plurality of high density meshes, by performing a CFD analysis, on the boundary conditions imposed 3D-CFD model. Finally, the method extracts a plurality of LA hemodynamic metrics of wall shear stress (WSS), that are possible indicators for progression of Atrial Fibrillation (AF), from the calculated mitral flow blood velocity, wherein the plurality of LA hemodynamic metrics comprising of time average wall shear stress (TAWSS), oscillatory shear index (OSI) and endothelial cell activation potential (ECAP) are indicators for progression of the AF.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
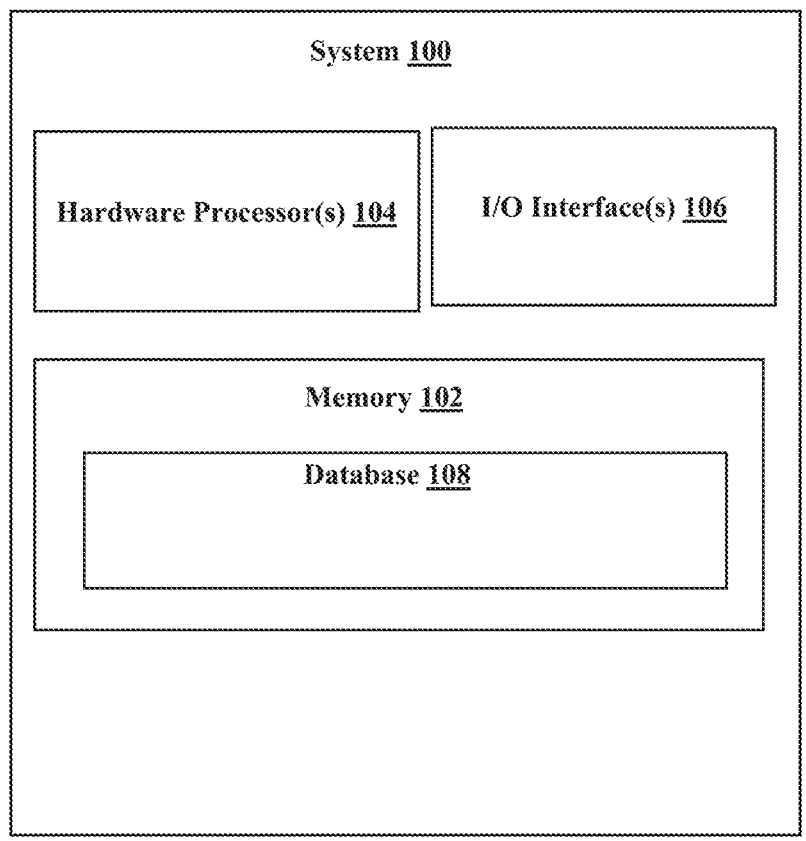
FIG. 1 is a functional block diagram of a system for determining progression of an atrial fibrillation (AF) based on hemodynamic metrics, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following embodiments described herein.

In Atrial Fibrillation (AF) apart from high frequency fibrillation of arterial wall, the AF is characterized with lack of active contraction of LA, referred to as atrial kick as discussed in literature (e.g., "D. Gupta, A. Shah, R. Giugliano, C. Ruff, et al. Left atrial structure and function in atrial fibrillation, European Heart Journal, vol: 35(22), pp: 1457-1465, 2014."). Changes in LA dynamics over prolonged period, as in case of a persistent AF cause structural and functional remodelling of the LA. Especially a structure in the LA known as a left atrial appendage (LAA) is known to aid in blood stasis due to the improper LA contraction and alteration in interatrial blood flow dynamics which consequently increases stroke risk. Conventionally the AF is detected mainly through ECG. However, several clinical studies suggests that hemodynamic analysis on the LA and the LAA are crucial for risk stratification of thromboembolic events. Computational fluid dynamics (CFD) is a potent tool that could evaluate subject specific structural changes associated with the LA remodeling and link with hemodynamic effect and predict chances of the thromboembolic events. Conventionally in the CFD models, the effect of AF on a cardiovascular system has not been modeled. Further in some conventional CFD models, express the pressure flow dynamical variation during the AF, but the effect of the AF on the cardiovascular system has not been modeled. Further in these models, evaluation of associated hemodynamic metrics and effect on the LA dynamics have not been considered.

The method and system for determining progression of the AF based on the hemodynamic metrics disclosed herein, analyzes the effect of the AF on various cardiovascular parameters like pressure flow dynamics at the LA and pressure flow dynamics at the LV as well as effect on the LA wall stress parameters for the AF variations. A 3D-CFD model is modelled from a plurality of medical scan images of a heart of a subject, and the AF variations are incorporated in a zero-dimensional (OD) lumped cardiovascular hemodynamic model along with a rhythm generator that generates the AF specific cardiac compliance and cardiac rhythms. The method and system enable improvement in understanding the AF progression that leads to the thromboembolic events.

An implementation of the method and system for determining progression of the atrial fibrillation (AF) based on the hemodynamic metrics is described further in detail with reference to FIGS. 1 through 7.

Referring now to the drawings, and more particularly to FIG. 1 through 7, where similar reference characters denote corresponding features consistently throughout the figures, there are shown preferred embodiments and these embodiments are described in the context of the following exemplary system and/or method.

FIG. 1 is a functional block diagram of a system 100 for determining progression of the AF based on the hemodynamic metrics, according to some embodiments of the present disclosure. In an embodiment the system 100 includes or is otherwise in communication with one or more hardware processors 104, communication interface device(s) or input/output (I/O) interface(s) 106 (also referred as interface(s)), and one or more data storage devices or memory 102 operatively coupled to the one or more hardware processors 104. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is/are configured to fetch and execute computer-readable instructions stored in the memory. In an embodiment, the system 100 can be implemented in a variety of computing systems, such as laptop computers, notebooks, hand-held devices (e.g., smartphones, tablet phones, mobile communication devices, and the like), workstations, mainframe computers, servers, a network cloud, and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

Figure 2:
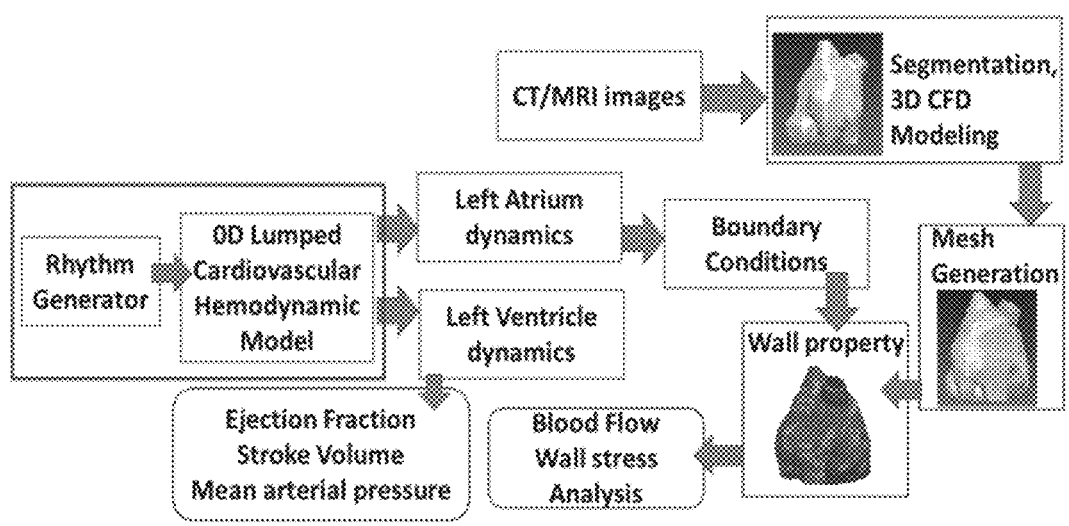
FIG. 2 illustrates a pipeline for a three-dimensional Computational Fluid Dynamics (3D-CFD) model and a zero-dimensional (OD) lumped cardiovascular hemodynamic model, for the system, for determining progression of the atrial fibrillation based on the hemodynamic metrics, in accordance with some embodiments of the present disclosure.

The memory 102 may include any computer-readable medium known in the art including, for example, volatile memory, such as static random-access memory (SRAM) and dynamic-random access memory (DRAM), and/or non-volatile memory, such as read only memory (ROM), erasable programmable ROM, flash memories, hard disks, optical disks, and magnetic tapes. In an embodiment, a database 108 is comprised in the memory 102, wherein the database 108 comprises information of the plurality of medical scan images. The memory 102 further comprises of a plurality of cardiovascular parameters, the hemodynamic metrics, a plurality of blood inflow boundary conditions and a plurality of blood outflow boundary condition, LA wall properties, and cardiac rhythms. The memory 102 further comprises plurality of module such as the 3D-CFD model, an Electrophysiology (EP) (not shown) module, a simplified Central Nervous system (CNS) (not shown), the OD lumped cardiovascular hemodynamic model along with the rhythm generator and the like as shown in FIG. 2 depicting process overview of the system 100. The above-mentioned technique(s) are implemented as at least one of a logically self-contained part of a software program, a self-contained hardware component, and/or, a self-contained hardware component with a logically self-contained part of a software program embedded into each of the hardware component (e.g., hardware processor 104 or memory 102) that when executed perform the method described herein. The memory 102 further comprises (or may further comprise) information pertaining to input(s)/output(s) of each step performed by the systems and methods of the present disclosure. In other words, input(s) fed at each step and output(s) generated at each step are comprised in the memory 102 and can be utilized in further processing and analysis.

Figure 3A:
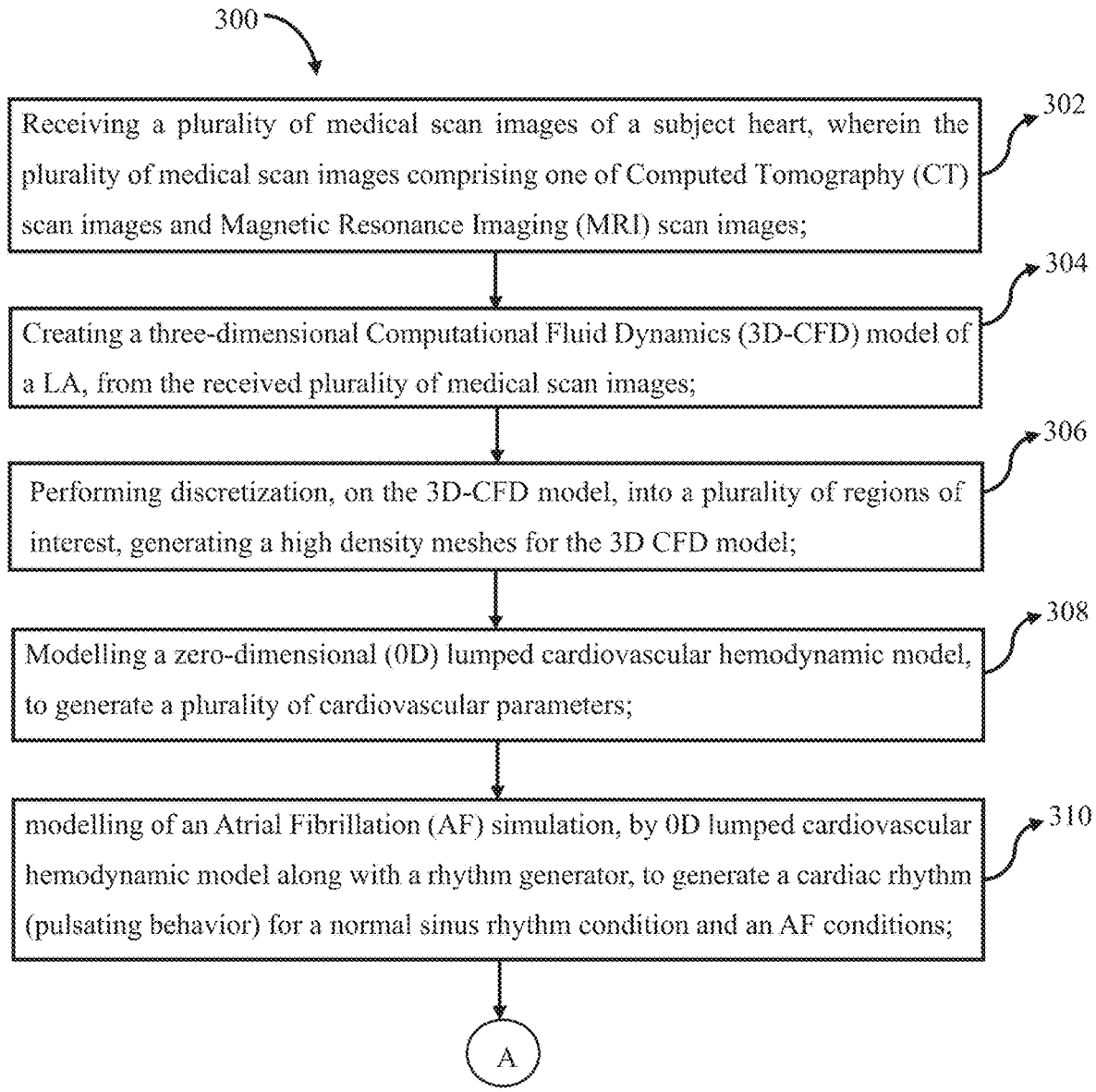
FIG. 3A and FIG. 3B are exemplary flow diagrams for a processor implemented method for determining progression of the atrial fibrillation (AF) based on the hemodynamic metrics, in accordance with some embodiments of the present disclosure.
Figure 3B:
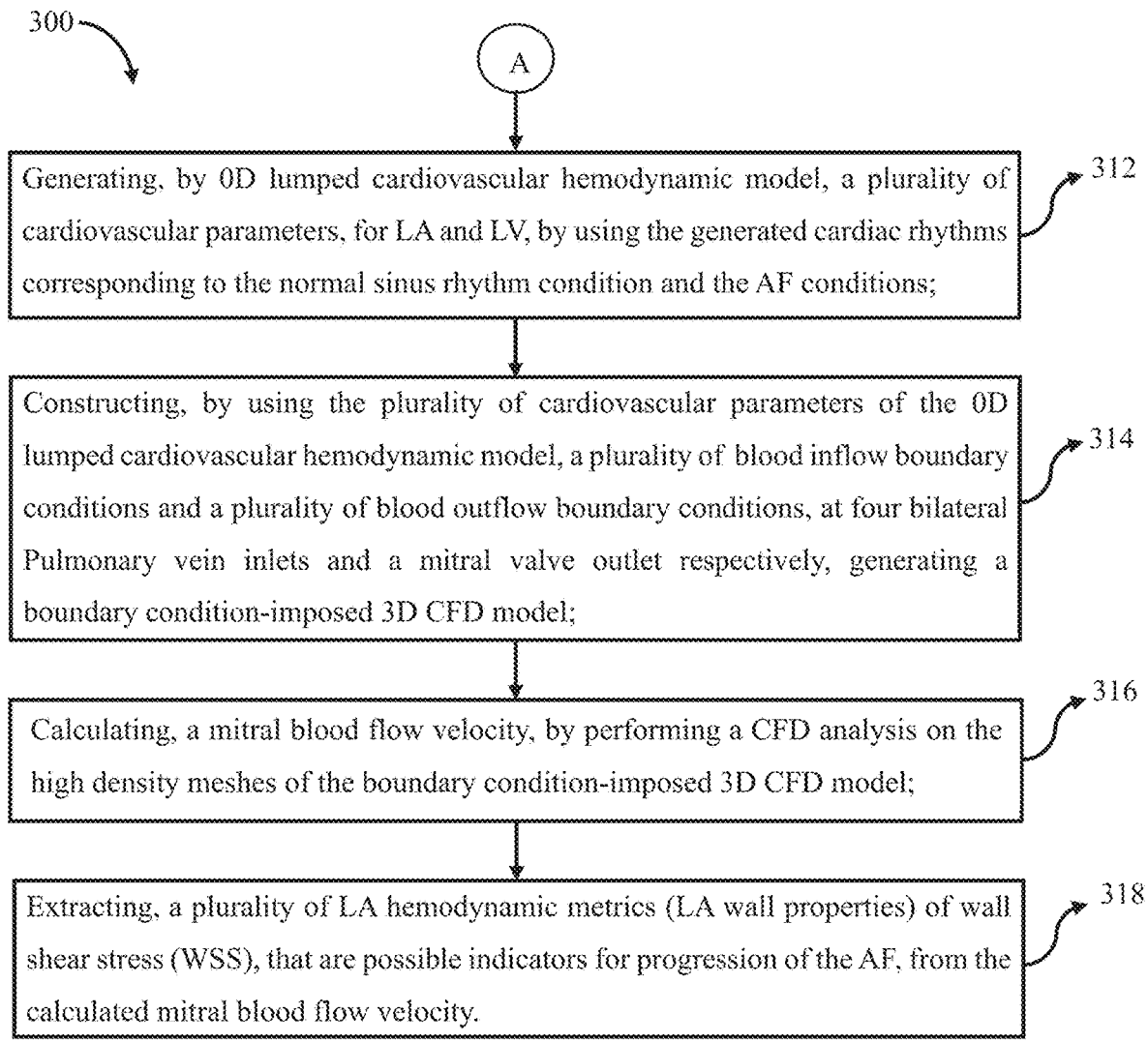

Functions of the components of system 100 are explained in conjunction with diagrams depicted in FIG. 2, FIG. 3A and, FIG. 3B for determining progression of the AF based on the hemodynamic metrics. In an embodiment, the system 100 comprises one or more data storage devices or the memory 102 operatively coupled to the processor(s) 104 and is configured to store instructions for execution of steps of the method depicted in FIG. 3A and FIG. 3B by the processor(s) or one or more hardware processors 104. The steps of the method of the present disclosure will now be explained with reference to the components or blocks of the system 100 as depicted in FIG. 1, the pipeline of 3D-CFD model and the OD lumped cardiovascular hemodynamic model in FIG. 2 and, the steps of the exemplary flow diagrams as depicted in FIG. 3A and FIG. 3B. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

FIG. 2, with reference to FIG. 1, illustrates a pipeline for the 3D-CFD model and the OD lumped cardiovascular hemodynamic model, for the system 100 for determining progression of the AF based on the hemodynamic metrics, in accordance with some embodiments of the present disclosure. The system 100, in FIG. 2, includes a CT/MRI images block comprising of the plurality of medical scan images of the heart of the subject. From the received plurality of the medical scan images, the 3D-CFD model is created, as shown in a segmentation and 3D-CFD Modelling block in FIG. 2 of the present disclosure. In a mesh generation block in FIG. 2 of the present disclosure, the system 100 generates a plurality of high density meshes, by performing discretization on the 3D-CFD model. The system 100 for determining progression of the AF based on the hemodynamic metrics, includes the OD lumped cardiovascular hemodynamic model block and the rhythm generator block. The AF is modelled by the OD lumped cardiovascular hemodynamic model along with the rhythm generator, to generate the cardiac rhythms for a normal sinus rhythm condition and AF conditions respectively. Further the plurality of cardiovascular parameters for the LA and the LV are generated from the generated cardiac rhythms corresponding to the normal sinus rhythm condition and the AF conditions respectively. The plurality of cardiovascular parameters for the LA and the LV corresponds to a Left Atrium dynamics block, and a Left Ventricle dynamics block are shown in the FIG. 2 of the present disclosure. At boundary conditions block in FIG. 2 of the present disclosure, the plurality of blood inflow boundary conditions and the plurality of blood outflow boundary conditions are created by using the plurality of cardiovascular parameters of the OD lumped cardiovascular hemodynamic model generating a boundary conditions imposed 3D-CFD model. Further at a wall property block in the FIG. 2 of the present disclosure, a CFD analysis is performed on the plurality of high density meshes of the 3D-CFD model, to calculate a mitral flow blood velocity, by using the boundary conditions imposed 3D-CFD model. The hemodynamic metrics comprises a plurality of LA hemodynamic metrics (LA wall properties) and a plurality of LV hemodynamic metrics. Further the plurality of LA hemodynamic metrics of wall shear stress (WSS) are calculated from the mitral flow blood velocity that are possible indicators for progression of the AF, as shown in the blood flow and wall stress analysis block in FIG. 2 of the present disclosure. The LV hemodynamic metrics such as an ejection fraction (EF), a stroke volume (SV) and a mean arterial pressure (MAP) are extracted from the Left Ventricle dynamics block as shown in FIG. 2 of the present disclosure.

FIG. 3A and FIG. 3B, with reference to FIGS. 1-2, are exemplary flow diagrams for a processor implemented a method 300 for determining progression of the AF based on the hemodynamic metrics, in accordance with some embodiments of the present disclosure. At step 302 of the present disclosure, the one or more hardware processors 104 receive, the plurality of medical scan images of the heart of the subject. The plurality of medical scan images can include Computed Tomography (CT) scan images or Magnetic Resonance Imaging (MRI) scan images.

Referring to steps of method 300, at step 304 of the present disclosure, one or more hardware processors 104 create, the three-dimensional Computational Fluid Dynamics (3D-CFD) model of the LA, from the received plurality of medical scan images. The method identifies a plurality of substructures, of the heart by a slice selection, in an axial, a coronal and a sagittal plane from the received plurality of medical scan images. Further the method identifies a plurality of path lines that are connecting centres of the plurality of substructures. Further the method performs segmentation, by using the plurality of the path lines, to generate a plurality of segmented sections. A cross sectional areas of the plurality of substructures are segmented based on selection of a slice criterion corresponding to optimal substructures of the LA. Then the method performs, a loft operation, on to the plurality of segmented sections and generates the 3D-CFD model of the LA. The loft operation performed on the plurality of segmented sections smoothens the 3D-CFD model of the LA for the CFD analysis. The generated 3D-CFD model of the LA comprising of four bilateral Pulmonary Veins (PVs) inlets, a LA chamber and outlet to a left ventricle (LV) via a mitral valve. The four bilateral PVs are a Right Superior Pulmonary Vein (RSPV), a Right Inferior Pulmonary Vein (RIPV), a Left superior Pulmonary Vein (LSPV) and a Left inferior Pulmonary Vein (LIPV).

Referring to steps of method 300, at step 306 of the present disclosure, one or more hardware processors 104 perform discretization, on the 3D-CFD model, into a plurality of regions of interest, generating the plurality of high density meshes.

At step 308 of the method 300, one or more hardware processors 104 model, the OD lumped cardiovascular hemodynamic model, to generate the plurality of cardiovascular parameters. The plurality of cardiovascular parameters comprises, a systemic artery flow, a pulmonary artery flow, the pressure flow dynamics at the LA (LA dynamics), the pressure flow dynamics at the LV (LV dynamics), a left atrium compliance corresponding to the LA dynamics, and a left ventricle compliance corresponding to the LV dynamics. The OD lumped cardiovascular hemodynamic model comprises of the Electrophysiology (EP) module (not shown), and the simplified Central Nervous system (CNS) (not shown). The OD lumped cardiovascular hemodynamic model (i) regulates the systemic artery flow and, the pulmonary artery flow (ii) captures and replicates the LA dynamics and the LV dynamics, and the volume dynamics during a cardiac cycle. The LA dynamics and the LV dynamics replication of the OD lumped cardiovascular hemodynamic model, at the LA and the LV that are expressed by a state space as:

$$P_{la} = \frac{1}{C_{la}(t)}\left[\frac{P_{la} - P_{pa}}{R_p} - U_{mi} \times \frac{P_{la} - P_{lv}}{R_{mi}} - C_{la}(t)P_{la}\right] \quad (1)$$

-continued $$P_{la} = \frac{1}{C_{lv}(t)}\left[U_{mi} \times \frac{P_{la} - P_{lv}}{R_{mi}} - U_{ao} \times \frac{P_{lv} - P_{sa}}{R_{ao}} - C_{lv}(t)P_{lv}\right] \quad (2)$$

where $P_{la}$, $P_{lv}$, $P_{sa}$ and $P_{pa}$ are pressure variables, capturing the LA dynamics and the LV dynamics at the LA and the LV, the systemic artery flow, the pulmonary artery flow respectively; $R_{mi}$, $R_{ao}$ are valvular resistance across the mitral valve, and aortic valves; $R_p$ is a vascular resistance; $C_{la}$, $C_{la}$ are LA compliance and LV compliance respectively; $U_{mi}$, $U_{ao}$ are control inputs for opening and closing of heart valves and t is a function of time that varies with each cardiac cycle.

The method for determining progression of the atrial fibrillation based on hemodynamic metrics, extracts LV hemodynamic metrics such as, the EF, the MAP and the stroke volume from the pressures variables that captured pressure flow dynamics at the LV (the LV dynamics), the systemic artery flow, the pulmonary artery flow respectively, to analyze general cardiovascular health of the heart.

Referring to steps of method 300, at step 310 of the present disclosure, the one or more hardware processors 104 model, the AF, by the 0D lumped cardiovascular hemodynamic model along with the rhythm generator, to generate the cardiac rhythms (pulsating behavior) for the normal sinus rhythm condition and the AF conditions respectively. The AF conditions includes a high frequency AF (HF-AF) rhythm condition and, a LA remodeled AF rhythm condition. The method of the present disclosure sequentially activates heart chambers of the 0D lumped cardiovascular hemodynamic model, by a plurality of time-varying compliance functions incorporated by the rhythm generator that generates AF specific compliance functions. The time varying compliance functions across right atrium $C_{ra}(t)$, left atrium $C_{la}(t)$, right ventricle $C_{rv}(t)$ and, left ventricle $C_{lv}(t)$, incorporated by the rhythm generator is mathematically represented as:

$$C_{ra}(t) = C_{min,ra} + 0.5 \times (C_{max,ra} - C_{min,ra})u(t) \quad (3)$$

$$C_{la}(t) = C_{min,la} + 0.5 \times C_{max,la} - C_{min,la})u(t - d_{la}) \quad (4)$$

$$C_i(t) = Ci \times u_v(t-d), i \in \{lv, rv\} \quad (5)$$

where $C_{min,ra}$, $C_{min,la}$ are minimum values of a right atrium (RA) compliance and a LA compliance respectively; $C_{max,ra}$, $C_{max,la}$ are maximum values of the RA compliance and the LA compliance respectively; $C_i$; $i \in \{lv, rv\}$ is a systolic compliance across the LV and the RV; $d_{la}$ and d represents the delay in activation of the LA and the LV with respect to the RA; $u(t)$ and $u_v(t)$ define activation functions at a predefined time (t) in the LA, the RA, and the LV and the RV respectively. The activation function at the t is mathematically expressed as:

$$u(t) = \begin{cases} 0, & 0 \le t < T_a \\ 1 - \cos\left(2\pi \times n_{af} \times \frac{t - T_a}{T - T_a}\right), & T_a \le t < T \end{cases} \quad (6)$$

$$u_v(t) = \begin{cases} 0.5 - 0.5\cos\left(\pi\frac{t}{T_1}\right), & 0 \le t < T_1 \\ 0.5 - 0.5\cos\left(\pi\frac{t - T_1}{T_2 - T_1}\right), & T_1 \le t < T_2 \\ 0, & T_2 \le t < T_{21} \end{cases} \quad (7)$$

where $T_a$ is an activation times across the RA; $T_1$, and $T_2$ are systolic and diastolic activation time instances of the cardiac cycle (T=60/HR) respectively; HR is the (cardiac rhythm) heart rate for a normal sinus rhythm; and $n_{af}$ is a decoupled factor of the LA with respect to the cardiac cycle, wherein under the normal sinus rhythm condition, $n_{af}$=1, such that the atrium and the ventricle pair operates synchronously.

The Atrial Fibrillation disrupts not only the normal sinus rhythm condition but also impact changes in mechanical properties of the LA and the LV. The changes in the mechanical properties of the LA and the LV in turn effects the overall functionality of the cardiovascular system. The method for determining progression of the AF based on the hemodynamic metrics, models the AF conditions, such as the HF-AF rhythm condition and the LA remodeled AF rhythm condition. The HF-AF rhythm condition is modelled by replicating high oscillation frequency at the LA without making any changes in the LA dynamics, which generates the cardiac rhythm corresponding to the HF-AF rhythm condition. The LA remodeled AF is modeled by changing the LA compliance that is seen in a chronic persistent AF, which generates the cardiac rhythm corresponding to the LA remodeled AF rhythm condition.

Referring to steps of method 300, at step 312 of the present disclosure, the one or more hardware processors 104, generate, by the 0D lumped cardiovascular hemodynamic model, the plurality of cardiovascular parameters, for the LA and the LV by using the generated cardiac rhythms, by using the step 308 of method 300 of the present disclosure. The generated cardiac rhythms are corresponding to the normal sinus rhythm condition and the AF conditions respectively.

Figure 4:
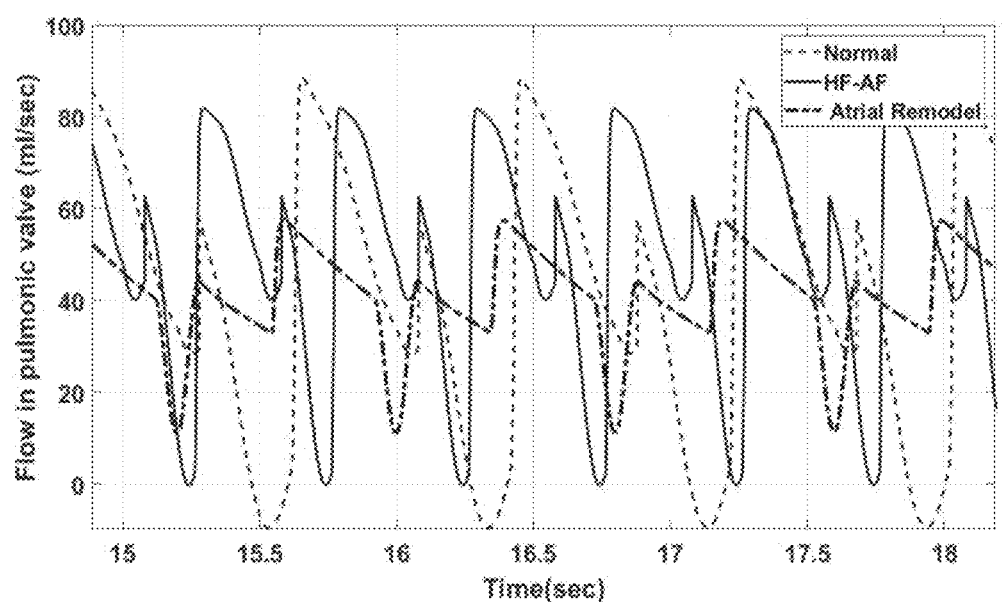
FIG. 4 illustrates a plot for blood inflow boundary conditions at four bilateral pulmonary vein inlets, for a normal sinus rhythm condition and AF conditions, in accordance with some embodiments of the present disclosure.

Referring to steps of method 300, at step 314 of the present disclosure, the one or more hardware processors 104 construct, by using the plurality of cardiovascular parameters of the 0D lumped cardiovascular hemodynamic model, the plurality of blood inflow boundary conditions and the plurality of blood outflow boundary conditions, at four bilateral pulmonary vein inlets and the mitral valve outlet respectively, generating a boundary conditions imposed 3D-CFD model. The 3D-CFD model requires the plurality of blood inflow boundary conditions and the plurality of blood outflow boundary conditions at the pulmonary veins and the mitral valve respectively. The method assigns the plurality of blood inflow boundary conditions at the four bilateral Pulmonary vein inlets and the plurality of blood outflow boundary conditions at the mitral valve outlet (mitral flow) by using the LA dynamics of the plurality of cardiovascular parameters obtained from equation (1) and equation (2) of the present disclosure. For the plurality of blood inflow boundary conditions, the total inflow was distributed at the four bilateral pulmonary vein inlets, according to proportion of their respective cross-sectional areas, wherein the proportions of the cross-sectional areas of the four bilateral pulmonary vein inlets are RSPV: 0.506 cm², RIPV: 1.742 cm², LSPV: 0.950 cm², and LIPV: 1.035 cm². The normal sinus rhythm condition, HF-AF rhythm condition and the LA remodeled AF rhythm condition are also interchangeably referred to as normal (healthy), HF-AF (high frequency) and atrial remodel respectively. The plurality of blood inflow boundary conditions at the four bilateral pulmonary vein inlets, for the normal sinus rhythm condition, the HF-AF rhythm condition and the LA remodeled AF rhythm condition is shown in FIG. 4 of the present disclosure. The variations in the plurality of blood inflow boundary conditions at the four bilateral pulmonary vein inlets for the HF-AF rhythm condition and the LA remodeled AF rhythm condition with respect to the normal sinus rhythm condition is evident from the FIG. 4. of the present disclosure.

At step 316 of the method 300, one or more hardware processors 104 calculate, by performing the CFD analysis, the mitral flow blood velocity, on the plurality of high density meshes of the boundary conditions imposed 3D-CFD model. The CFD analysis is governed by Navier-Stokes equations that represents combinations of continuity (mass balance) and momentum balance equations defined as:

$$\rho\left(\frac{\partial v}{\partial t}+v.\nabla v\right)=-\nabla p+\mu\nabla^2 v+f;\ \nabla.v=0, \quad (8)$$

where v is a blood velocity vector, p is a blood density vector and, f is a body force that was acting on fluid per unit mass at the time t.

Blood is considered as a Newtonian fluid with constant density and viscosity of 1060 kg·m³ and 0.004 pa·s respectively. The Navier-Stokes equations, for performing the CFD analysis, are computed at the plurality of high density meshes, with the plurality of blood inflow boundary conditions at the four bilateral Pulmonary vein inlets and the plurality of blood outflow boundary conditions at the mitral valve outlet, for (i) the normal sinus rhythm condition, (ii) the HF-AF rhythm condition and, (iii) the LA remodeled AF rhythm condition. The mitral flow blood velocity (flow rate), for the performed CFD analysis is shown in the FIG. 5. In the FIG. 5, normal mitral flow blood velocity corresponding to the normal sinus rhythm has biphasic nature with two peaks termed as E wave (passive filling in FIG. 5) and A wave (active contraction in FIG. 5). The E wave represents a passive blood flow from the LA to the LV, while the A wave reflects blood flow generated by an active atrial contraction. As the AF affects the active atrial contraction due to compromised atrial contractility, with progression of the AF the A wave morphology changes in the mitral flow and the mitral flow blood velocity that can be noticed in the FIG. 5 for (i) the normal sinus rhythm condition, (ii) the HF-AF rhythm condition and, (iii) the LA remodeled AF rhythm condition.

At step 318 of the method 300, one or more hardware processors 104 extract, the plurality of LA hemodynamic metrics (LA wall properties) of wall shear stress (WSS) that are possible indicators for progression of the AF, from the calculated mitral flow blood velocity, wherein the LA hemodynamic metrics of the WSS, such as time average wall shear stress (TAWSS), oscillatory shear index (OSI) and endothelial cell activation potential (ECAP) are the possible indicators for progression of the AF. The TAWSS $$\left(TWASS=\frac{1}{T}\int_0^T |WSS|dt\right)$$

is used to determine magnitude of sheer stress exerted on the arterial wall over the cardiac cycle. T is the cardiac cycle. Low values of the TAWSS indicates formation of fatty atherogenic deposits whereas high values of the TAWSS can lead to the thromboembolic events. The OSI $$\left(OSI=0.5\left[1-\left(\frac{\left|\int_0^T WSSdt\right|}{\int_0^T |WSS|DT}\right)\right]\right)$$

is a dimensionless LA hemodynamic parameter commonly used to identify the atheroprone regions while the ECAP is the ratio of the OSI to the TAWSS and points towards a thrombogenic prone region. Relative residence time $$(RRT)\left(RRT=\frac{1}{\frac{1}{T}\int_0^T |WSS|dt}\right)$$

identifies region that high particle residence time befalls.

Experimental Results

Figure 5:
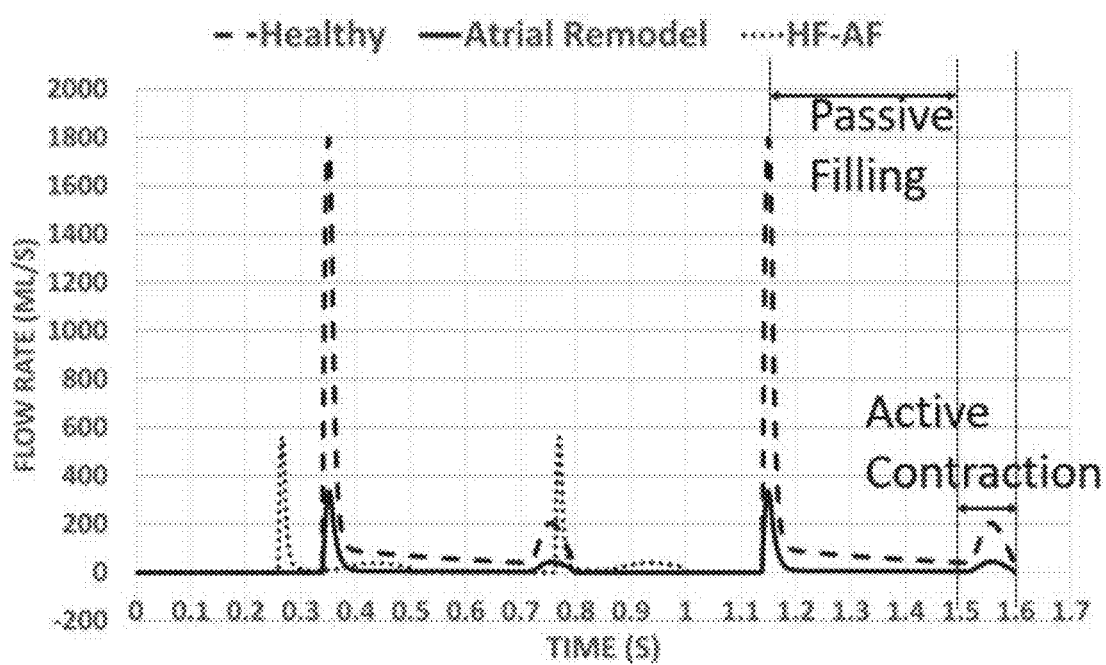
FIG. 5 illustrates a plot for a mitral flow blood velocity, for the normal sinus rhythm condition and the AF conditions, in accordance with some embodiments of the present disclosure.
Figure 6:
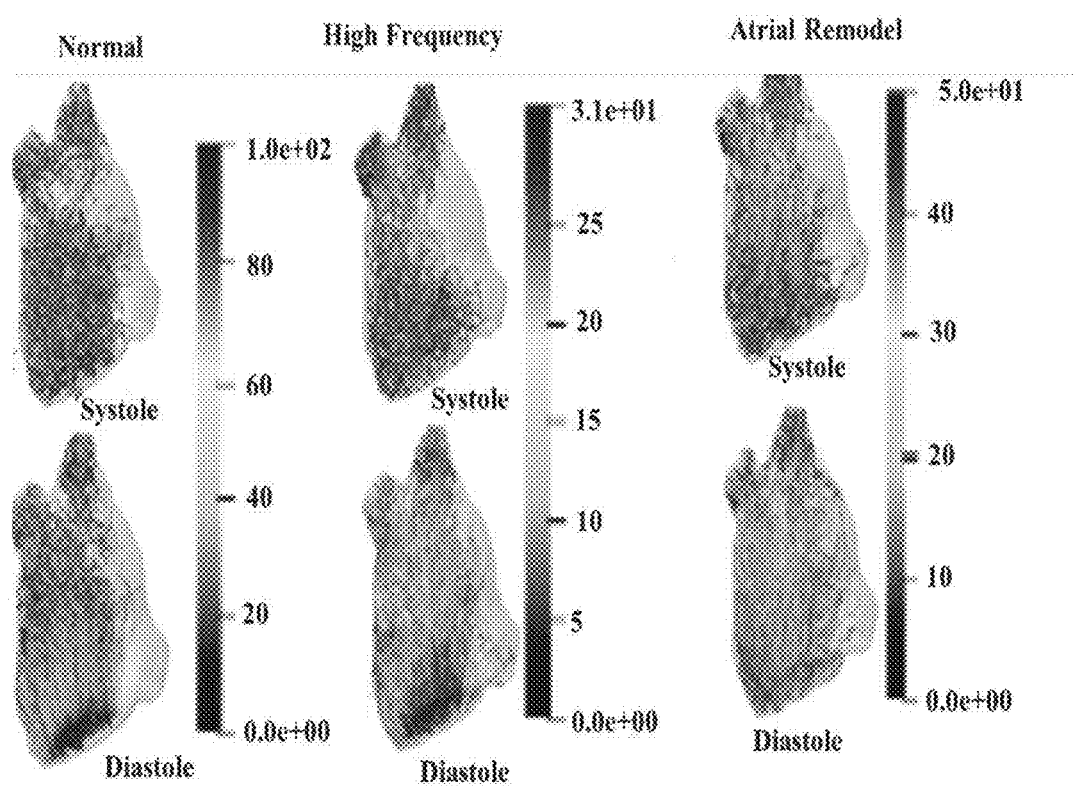
FIG. 6 illustrates a plot for the mitral flow blood velocity of LA, for the normal sinus rhythm condition and the AF conditions, in accordance with some embodiments of the present disclosure.

The system and method of the present disclosure presents the LA dynamics and the LV dynamics, the mitral flow blood velocity and the plurality of LA hemodynamic metrics (LA wall properties) of the WSS, for (i) the normal sinus rhythm condition, (ii) the HF-AF rhythm condition and, (iii) the LA remodeled AF rhythm condition. The most common indicator in the plurality of LA hemodynamics is the change in the mitral flow and the mitral flow blood velocity in the mitral valve due to the compromised atrial contraction phase and disturbances changes in the A wave, as shown in FIG. 5 of the present disclosure. The A wave for the HF-AF rhythm condition diminishes and in case of the LA remodeled AF rhythm condition the A wave is almost absent due to lack of the atrial kick, as shown in FIG. 5. The mitral flow blood velocity of LA for (i) the normal sinus rhythm condition, (ii) the HF-AF rhythm condition and, (iii) the LA remodeled AF rhythm condition is shown in FIG. 6. In the FIG. 6, it is noticed that with respect to the normal sinus rhythm condition, there is an apparent change in both the mitral flow and the mitral flow blood velocity for the HF-AF rhythm condition and for the LA remodeled AF rhythm condition. Changes in the mitral flow and the mitral flow blood velocity were observed in a systole and a diastole and observed that are more prominent at the mitral valve region during a ventricular diastole.

Figure 7:
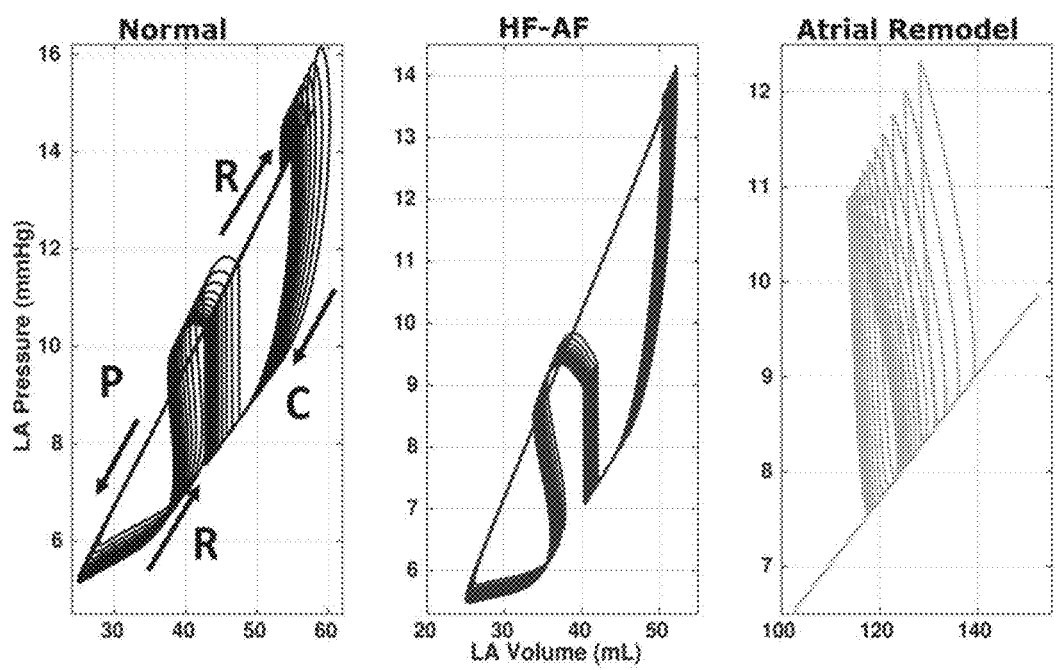
FIG. 7 illustrates a plot for pressure dynamics and volume dynamics plot of the LA, for the normal sinus rhythm condition and the AF conditions, in accordance with some embodiments of the present disclosure.

Pressure dynamics and volume dynamics plot of the LA are shown in the FIG. 7 of the present disclosure. Normal LA pressure dynamics and the volume dynamics depicts three phases of the LA functionality as shown in FIG. 7 of the present disclosure. In a first phase during LV contraction and isovolumetric relaxation, the LA acts as a reservoir (marked CR' in FIG. 7) storing incoming blood from the PVs. Next, is the passive filling phase, where the LA acts as a conduit ('C') followed by the active contraction pump ('P') phase or the atrial kick (A wave) at the end diastolic phase filling up the LV. The distinctive phases generate the typical dual filling shape of the pressure dynamics and the volume dynamics. In the HF-AF rhythm condition, shape of the loop is maintained with slightly lower volume at the active filling phase due to compromised active contraction phase. In the LA remodeled AF rhythm condition, shows a very distinctive shift in the pressure volume pattern. Due to absence of the atrial kick, the active filling phase is almost absent. Also, there is a large increase in the LA volume dynamics, which in turn enlarges size of the LA and further compromises contractility property that is evident in a persistent AF.

Although the AF is predominantly the LA disorder, the generic health of the cardiovascular system is assessed by the LV function like the SV, the EF, the MAP. Conventional treatment and therapy provided for the AF generally focuses on keeping the LV functionality under control. Hence analysis of the AF only on the LA parameters are incomplete as in prolonged AF, even at lower atrium fibrillation frequency, cardiac chambers (both atrium and ventricle) are prone to changes in contractility and compliance. The LV hemodynamic metrics for (i) the normal sinus rhythm condition, (ii) the HF-AF rhythm condition and, (iii) the LA remodeled AF rhythm condition are listed in a Table I. There are noticeable variations in the EF, a cardiac output (CO), the SV, the end systolic pressure volume ratio (ESPVR) correlating with ventricular muscle stiffness and end diastolic pressure volume ratio (EDPVR) correlating with contractility. For the HF-AF rhythm condition, due to increase in the cardiac rhythm, the CO is elevated but the SV is reduced due to reduction in the end diastolic volume. Whereas for the LA remodeled AF rhythm condition due to enlarged in size of the LA, there is increased end diastolic flow and volume. Hypertension is a common trait associated with AF. In the HF-AF rhythm condition, the MAP is elevated due to increase in the systolic pressure, mostly contributed by high cardiac rhythm. This effect is rather damped in the LA remodeled AF rhythm condition and arterial pressure is equivalent to normal. Similarly, the EF is slightly compromised in the HF-AF rhythm condition, but no such trend is observed in the LA remodeled AF rhythm condition. The changes in the ESPVR and the EDPVR are negligible, the changes do not reflect much about changes in LV contractility, the difference is mostly due to end diastolic volumetric changes associated with increased LA size and increased end systolic pressure for high frequency cases.

TABLE I

| Metric | Normal | HF-AF | Atrial remodel |
|---|---|---|---|
| CO (l/min) | 5.25 | 6.31 | 5.40 |
| SV (ml) | 82.35 | 57.19 | 91.82 |
| EF (%) | 54.10 | 44.80 | 54.30 |
| MAP (mmHg) | 86.34 | 107.60 | 88.15 |
| ESPVR | 2.15 | 2.09 | 2.11 |
| EDPVR | 0.072 | 0.070 | 0.079 |

Table II of the present disclosure lists the LA hemodynamic metrics. For the HF-AF rhythm condition in the Table II, the TAWSS and the OSI vales, making more prone to blood statis and the thromboembolic events. The RRT and the ECAP values similarly shows a slightly increased trend for both the HF-AF rhythm condition and the LA remodeled AF rhythm condition compared to the normal sinus rhythm condition. An average ECAP value for the HF-AF rhythm condition is near a threshold level (0.14) of the thromboembolic events. In terms of the hemodynamic parameter of the LA, the HF-AF rhythm condition is noticed to be more susceptible to the thromboembolic events.

TABLE II

| Metric | Normal | HF-AF | Atrial remodel |
|---|---|---|---|
| TAWSS (dyne/cm2) | 4.0437 | 1.4695 | 2.5189 |
| OSI | 0.1815 | 0.0742 | 0.0911 |
| RRT (cm2/dyne) | 0.4826 | 1.0442 | 0.6174 |
| ECAP (cm2/dyne) | 0.0851 | 0.129 | 0.0962 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The method and system for determining progression of atrial fibrillation (AF) based on hemodynamic metrics, analyze the effect of the AF on various cardiovascular parameters like the LA and the LV pressure flow dynamics as well as effect on the LA wall stress parameters for the AF variations. A 3D-CFD model is modelled from the medical scan images of the heart and the AF variations are incorporated in the zero-dimensional (OD) lumped cardiovascular hemodynamic model along with the novel rhythm generator that generates the AF specific cardiac compliances and cardiac rhythms. The method and system for determining progression of atrial fibrillation based on hemodynamic metrics, using 3D-CFD model and OD lumped cardiovascular hemodynamic model along with the rhythm generator, used to improve in understanding the AF progression that leads to the thromboembolic events.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
   receiving, by one or more hardware processors, a plurality of medical scan images of a heart of a subject;
   creating, by the one or more hardware processors, a three-dimensional Computational Fluid Dynamics (3D-CFD) model of a Left Atrium (LA), from the received plurality of medical scan images;
   performing, by the one or more hardware processors, discretization on the 3D-CFD model, into a plurality of regions of interest, generating a plurality of high density meshes;
   modelling, by the one or more hardware processors, a zero-dimensional (0D) lumped cardiovascular hemodynamic model, to generate a plurality of cardiovascular parameters, wherein the plurality of cardiovascular parameters comprises, a systemic artery flow, a pulmonary artery flow, pressure flow dynamics at the LA (LA dynamics), pressure flow dynamics at a left ventricle (LV dynamics), a left atrium compliance corresponding to the LA dynamics and, a left ventricle compliance corresponding to the LV dynamics;
   modelling, by the 0D lumped cardiovascular hemodynamic model along with a rhythm generator controlled by the one or more hardware processors, an Atrial Fibrillation (AF) to generate cardiac rhythms for a normal sinus rhythm condition and AF conditions, wherein the AF conditions comprises a high frequency AF (HF-AF) rhythm condition and, a LA remodeled AF rhythm condition;
   generating, by the 0D lumped cardiovascular hemodynamic model executed by the one or more hardware processors, the plurality of cardiovascular parameters, for the LA and the LV, by using the generated cardiac rhythms corresponding to the normal sinus rhythm condition and the AF conditions, wherein the 0D lumped cardiovascular hemodynamic model heart chambers are activated sequentially by a plurality of time-varying compliance functions incorporated by the rhythm generator that generates AF specific compliance functions, wherein the time varying compliance functions across right atrium $C_{ra}(t)$, left atrium $C_{la}(t)$, right ventricle $C_{rv}(t)$ and, left ventricle $C_{lv}(t)$, incorporated by the rhythm generator is mathematically represented as:

$$C_{ra}(t) = C_{min,ra} + 0.5 \times (C_{max,ra} - C_{min,ra}) u(t)$$

$$C_{la}(t) = C_{min,la} + 0.5 \times C_{max,la} - C_{min,la}) u(t-d_{la})$$

$$C_i(t) = Ci \times u_v(t-d), i \in \{lv, rv\}$$

where $C_{min,ra}$ corresponds to minimum values of a Right Atrium (RA) compliance; $C_{min,la}$ corresponds to a minimum values of the LA compliance; $C_{max,ra}$ corresponds to maximum values of RA compliance; $C_{max,la}$ corresponds to the maximum values of the LA compliance r; $C_i$; $i \in \{lv, rv\}$ is a systolic compliance across the LV and the RV; $d_{la}$ and d represents the delay in activation of the LA and the LV with respect to the RA; $u(t)$ and $u_v(t)$ define activation functions at a predefined time (t) in the LA, the RA, the LV and the RV, wherein the activation functions at the t is mathematically expressed as:

$$u(t) = \begin{cases} 0, & 0 \le t < T_a \\ 1 - \cos\left(2\pi \times n_{af} \times \frac{t-T_a}{T-T_a}\right), & T_a \le t < T \end{cases}$$

$$u_v(t) = \begin{cases} 0.5 - 0.5 \cos\left(\pi \frac{t}{T_1}\right), & 0 \le t < T_1 \\ 0.5 - 0.5 \cos\left(\pi \frac{t-T_1}{T_2-T_1}\right), & T_1 \le t < T_2 \\ 0, & T_2 \le t < T_{21} \end{cases}$$

where $T_a$ is an activation times across the RA; $T_1$, and $T_2$ are systolic and diastolic activation time instances of the cardiac cycle (T=60/HR); HR is the cardiac rhythm for the normal sinus rhythm; and nor is a decoupled factor of the LA with respect to the cardiac cycle, wherein under the normal sinus rhythm condition, $n_{af}=1$, such that the atrium and the ventricle pair operates synchronously;

constructing, by the one or more hardware processors, a plurality of blood inflow boundary conditions at a bilateral pulmonary vein inlets and a plurality of blood outflow boundary conditions at a mitral valve outlet, by using the plurality of cardiovascular parameters of the 0 D lumped cardiovascular hemodynamic model, generating a boundary conditions imposed 3D-CFD model;

calculating, by the one or more hardware processors, a mitral flow blood velocity, by performing a CFD analysis on the plurality of high density meshes of the boundary conditions imposed 3D-CFD model; and extracting, by the one or more hardware processors, a plurality of LA hemodynamic metrics of wall shear stress (WSS) that are possible indicators for progression of Atrial Fibrillation (AF), from the calculated mitral flow blood velocity, wherein the plurality of LA hemodynamic metrics comprises time average wall shear stress (TAWSS), oscillatory shear index (OSI) and endothelial cell activation potential (ECAP) are indicators for progression of the AF.

2. The processor implemented method of claim 1, wherein the plurality of medical scan images comprises one of Computed Tomography (CT) scan images and Magnetic Resonance Imaging (MRI) scan images, and wherein creating the 3D-CFD model of the LA, from the received plurality of medical scan images comprises:
- identifying, by a slice selection in an axial, a coronal and a sagittal plane, a plurality of substructures in the heart, from the plurality of medical scan images;
- identifying a plurality of path lines that are connecting centres of the plurality of substructures;
- performing segmentation, by using the plurality of the path lines, to generate a plurality of segmented sections, wherein cross-sectional areas of the plurality of substructures are segmented based on selection of a slice criterion corresponding to optimal substructures of the LA; and
- performing a loft operation, on to the plurality of segmented sections, generating the 3D-CFD model of the LA, wherein the loft operation performed on the plurality of segmented sections smoothens the 3D-CFD model of the LA for the CFD analysis, wherein the CFD analysis is governed by Navier-Stokes equations that represents combinations of continuity (mass balance) and momentum balance equations.

3. The processor implemented method of claim 2, wherein the generated 3D-CFD model of the LA comprises four bilateral Pulmonary Veins (PVs) inlets, a LA chamber and outlet to a left ventricle (LV) via a mitral valve, wherein the four bilateral PVs comprises a Right Superior Pulmonary Vein (RSPV), a Right Inferior Pulmonary Vein (RIPV), a Left superior Pulmonary Vein (LSPV) and a Left inferior Pulmonary Vein (LIPV).

4. The processor implemented method of claim 1, wherein the OD lumped cardiovascular hemodynamic model (i) regulates the systemic artery flow and, the pulmonary artery flow (ii) captures and replicates the LA dynamics and the LV dynamics, and volume dynamics during a cardiac cycle, wherein the LA dynamics and the LV dynamics replication of the OD lumped cardiovascular hemodynamic model at the LA and the LV, is expressed by a state space as:

$$P_{la} = \frac{1}{C_{la}(t)}\left[\frac{P_{la} - P_{pa}}{R_p} - U_{mi} \times \frac{P_{la} - P_{lv}}{R_{mi}} - C_{la}(t)P_{la}\right]$$

$$P_{la} = \frac{1}{C_{la}(t)}\left[\frac{P_{la} - P_{pa}}{R_p} - U_{mi} \times \frac{P_{la} - P_{lv}}{R_{mi}} - C_{la}(t)P_{la}\right]$$

where $P_{la}$, $P_{lv}$, $P_{sa}$, and $P_{pa}$ are pressure variables, capturing the LA dynamics and the LV dynamics, the systemic artery flow, the pulmonary artery flow; $R_{mi}$, $R_{ao}$ are valvular resistance across a mitral valve, and aortic valve; $R_p$ is a vascular resistance; $C_{la}$, $C_{la}$ are the LA compliance and the LV compliance; $U_{mi}$, $U_{ao}$ are control inputs for opening and closing of heart valves and t is a function of time that varies with each cardiac cycle.

5. The processor implemented method of claim 4, wherein the pressures variables that captured the LV dynamics, the systemic artery flow, the pulmonary artery flow extracts a plurality of LV hemodynamic metrics, wherein the plurality of LV hemodynamic metrics comprises an ejection fraction (EF), a mean arterial pressure (MAP) and a stroke volume, to analyze general cardiovascular health of the heart.

6. The processor implemented method of claim 1, wherein the HF-AF rhythm condition is modelled by replicating high oscillation frequency at the LA, without making any changes in the LA dynamics, which generates the cardiac rhythm corresponding to the HF-AF rhythm condition, and wherein the LA remodeled AF is modeled by changing the LA compliance that is seen in a chronic persistent AF, which generates the cardiac rhythm corresponding to the LA remodeled AF rhythm condition.

7. A system, comprising:
- a memory storing instructions;
- one or more communication interfaces; and
- one or more hardware processors coupled to the memory via the one or more communication interfaces, wherein the one or more hardware processors are configured by the instructions to:
  - receive a plurality of medical scan images of a heart of a subject;
  - create a three-dimensional Computational Fluid Dynamics (3D-CFD) model of a Left Atrium (LA), from the received plurality of medical scan images;
  - perform discretization on the 3D-CFD model, into a plurality of regions of interest, generating a plurality of high density meshes;
  - model a zero-dimensional (OD) lumped cardiovascular hemodynamic model, to generate a plurality of cardiovascular parameters, wherein the plurality of cardiovascular parameters comprises, a systemic artery flow, a pulmonary artery flow, pressure flow dynamics at the LA (LA dynamics) and pressure flow dynamics at a left ventricle (LV dynamics), a left atrium compliance corresponding to the LA dynamics and, a left ventricle compliance corresponding to the LV dynamics;
  - model by the OD lumped cardiovascular hemodynamic model along with a rhythm generator an Atrial Fibrillation (AF) to generate cardiac rhythms for a normal sinus rhythm condition and AF conditions, wherein the AF conditions comprises a high frequency AF (HF-AF) rhythm condition and, a LA remodeled AF rhythm condition;
  - generate by the OD lumped cardiovascular hemodynamic model, the plurality of cardiovascular parameters, for the LA and the LV, by using the generated cardiac rhythms corresponding to the normal sinus rhythm condition and the AF conditions, wherein the OD lumped cardiovascular hemodynamic model heart chambers are activated sequentially by a plurality of time-varying compliance functions incorporated by the rhythm generator that generates AF specific compliance functions, wherein the time varying compliance functions across right atrium $C_{ra}(t)$, left atrium $C_{la}(t)$, right ventricle $C_{rv}(t)$ and, left ventricle $C_{lv}(t)$, incorporated by the rhythm generator is mathematically represented as:

$$C_{ra}(t) = C_{min,ra} + 0.5 \times (C_{max,ra} - C_{min,ra})u(t)$$

$$C_{la}(t) = C_{min,la} + 0.5 \times (C_{max,la} - C_{min,la})u(t-d_{la})$$

$$C_i(t)) = Ci \times u_v(t-d), i \in \{lv, rv\}$$

where $C_{min,ra}$ corresponds to minimum values of a Right Atrium (RA) compliance; $C_{min,la}$ corresponds to a minimum values of the LA compliance; $C_{max,ra}$ corresponds to maximum values of RA compliance; $C_{max,la}$ corresponds to the maximum values of the LA compliance r; $C_i$; i∈ {lv, rv} is a systolic compliance across the LV and the RV; d, and d represents the delay in activation of the LA and the LV with respect to the RA; u(t) and $u_v(t)$ define activation functions at a predefined time (t) in the LA, the RA, the LV and the RV, wherein the activation functions at the t is mathematically expressed as:

$$u(t) = \begin{cases} 0, & 0 \le t < T_a \\ 1 - \cos\left(2\pi \times n_{af} \times \frac{t-Ta}{T-T_a}\right), & T_a \le t < T \end{cases}$$

$$u_v(t) = \begin{cases} 0.5 - 0.5 \cos\left(\pi \frac{t}{T_1}\right), & 0 \le t < T_1 \\ 0.5 - 0.5 \cos\left(\pi \frac{t-T_1}{T_2-T_1}\right), & T_1 \le t < T_2 \\ 0, & T_2 \le t < T_{21} \end{cases}$$

where $T_a$ is an activation times across the RA; $T_1$, and $T_2$ are systolic and diastolic activation time instances of the cardiac cycle (T=60/HR); HR is the cardiac rhythm for the normal sinus rhythm; and $n_{af}$ is a decoupled factor of the LA with respect to the cardiac cycle, wherein under the normal sinus rhythm condition, $n_{af}=1$, such that the atrium and the ventricle pair operates synchronously;

construct a plurality of blood inflow boundary conditions at a bilateral pulmonary vein inlets and a plurality of blood outflow boundary conditions at a mitral valve outlet, by using the plurality of cardiovascular parameters of the OD lumped cardiovascular hemodynamic model, generating a boundary conditions imposed 3D-CFD model;

calculate a mitral flow blood velocity, by performing a CFD analysis, on the on the plurality of high density meshes of the boundary conditions imposed 3D-CFD model; and extract a plurality of LA hemodynamic metrics of wall shear stress (WSS) that are possible indicators for progression of Atrial Fibrillation (AF), from the calculated mitral flow blood velocity, wherein the LA hemodynamic metrics comprises time average wall shear stress (TAWSS), oscillatory shear index (OSI) and endothelial cell activation potential (ECAP) are indicators for progression of the AF.

8. The system of claim 7, wherein the plurality of medical scan images comprises one of Computed Tomography (CT) scan images and Magnetic Resonance Imaging (MRI) scan images, and wherein the 3D-CFD model of the LA, from the received plurality of medical scan images comprises:

identifying, by a slice selection, in an axial, a coronal and a sagittal plane, a plurality of substructures in the heart, from the plurality of medical scan images;

identifying a plurality of path lines that are connecting centres of the plurality of substructures;

performing segmentation, by using the plurality of the path lines, to generate a plurality of segmented sections, wherein cross-sectional areas of the plurality of substructures are segmented based on selection of slice criterion corresponding to optimal substructures of the LA; and performing a loft operation, on to the plurality of segmented sections, generating the 3D-CFD model of the LA, wherein the loft operation performed on the plurality of segmented sections smoothens the 3D-CFD model of the LA for the CFD analysis, wherein the CFD analysis is governed by Navier-Stokes equations that represents combinations of continuity (mass balance) and momentum balance equations.

9. The system of claim 8, wherein the generated 3D-CFD model of the LA comprises four bilateral Pulmonary Veins (PVs) inlets, a LA chamber and outlet to a left ventricle (LV) via a mitral valve, wherein the four bilateral PVs comprises a Right superior Pulmonary Vein (RSPV), a Right inferior Pulmonary Vein (RIPV), a Left superior Pulmonary Vein (LSPV) and a Left inferior Pulmonary Vein (LIPV).

10. The system of claim 7, wherein the OD lumped cardiovascular hemodynamic model (i) regulates the systemic artery flow and, the pulmonary artery flow (ii) captures and replicates the LA dynamics and the LV dynamics, and volume dynamics during a cardiac cycle, wherein the LA dynamics and the LV dynamics replication of the OD lumped cardiovascular hemodynamic model at the LA and the LV, is expressed by a state space as:

$$P_{la} = \frac{1}{C_{la}(t)}\left[\frac{P_{la}-P_{pa}}{R_p} - U_{mi} \times \frac{P_{la}-P_{lv}}{R_{mi}} - C_{la}(t)P_{la}\right]$$

$$P_{la} = \frac{1}{C_{la}(t)}\left[\frac{P_{la}-P_{pa}}{R_p} - U_{mi} \times \frac{P_{la}-P_{lv}}{R_{mi}} - C_{la}(t)P_{la}\right]$$

where $P_{la}$, $P_{lv}$, $P_{sa}$, and $P_{pa}$ are pressure variables, capturing the LA dynamics and the LV dynamics, the systemic artery flow, the pulmonary artery flow; $R_{mi}$, $R_{ao}$ are valvular resistance across a mitral valve, and aortic valve; Ry is a vascular resistance; $C_{la}$, $C_{la}$ are the LA compliance and the LV compliance; $U_{mi}$, $U_{ao}$ are control inputs for opening and closing of heart valves and t is a function of time that varies with each cardiac cycle.

11. The system of claim 10, wherein the pressures variables that captured the LV dynamics, the systemic artery flow, the pulmonary artery flow, extracts a plurality of LV hemodynamic metrics, wherein the plurality of LV hemodynamic metrics comprises an ejection fraction (EF), a mean arterial pressure (MAP) and a stroke volume, to analyze general cardiovascular health of the heart.

12. The system of claim 7, wherein the HF-AF rhythm condition is modelled by replicating high oscillation frequency at the LA, without making any changes in the LA dynamics, which generates the cardiac rhythm corresponding to the HF-AF rhythm condition, and wherein the LA remodeled AF is modeled by changing the LA compliance that is seen in a chronic persistent AF, which generates the cardiac rhythm corresponding to the LA remodeled AF rhythm condition.

13. One or more non-transitory machine-readable information storage mediums comprising one or more instructions which when executed by one or more hardware processors cause:

receiving a plurality of medical scan images of a heart of a subject;

creating a three-dimensional Computational Fluid Dynamics model of a Left Atrium (LA), from the received plurality of medical scan images;

performing discretization on the 3D-CFD model, into a plurality of regions of interest, generating a plurality of high density meshes;

modelling a zero-dimensional lumped cardiovascular hemodynamic model, to generate a plurality of cardiovascular parameters, wherein the plurality of cardiovascular parameters comprises, a systemic artery flow, a pulmonary artery flow, pressure flow dynamics at the LA (LA dynamics), pressure flow dynamics at a left ventricle (LV dynamics), a left atrium compliance corresponding to the LA dynamics and, a left ventricle compliance corresponding to the LV dynamics;

modelling, by the OD lumped cardiovascular hemodynamic model along with a rhythm generator, an Atrial Fibrillation (AF) to generate cardiac rhythms for a normal sinus rhythm condition and AF conditions, wherein the AF conditions comprises a high frequency AF (HF-AF) rhythm condition and, a LA remodeled AF rhythm condition;

generating, by the OD lumped cardiovascular hemodynamic model, the plurality of cardiovascular parameters, for the LA and the LV, by using the generated cardiac rhythms corresponding to the normal sinus rhythm condition and the AF conditions, wherein the 0 D lumped cardiovascular hemodynamic model heart chambers are activated sequentially by a plurality of time-varying compliance functions incorporated by the rhythm generator that generates AF specific compliance functions, wherein the time varying compliance functions across right atrium $C_{ra}(t)$, left atrium $C_{la}(t)$, right ventricle $C_{rv}(t)$ and, left ventricle $C_{lv}(t)$, incorporated by the rhythm generator is mathematically represented as:

$$C_{ra}(t)=C_{min,ra}+0.5\times(C_{max,ra}-C_{min,ra})u(t)$$

$$C_{la}(t)=C_{min,la}+0.5\times C_{max,la}-C_{min,la})u(t-d_{la})$$

$$C_i(t))=Ci\times u_v(t-d), i\in \{lv,rv\}$$

where $C_{min,ra}$ corresponds to minimum values of a Right Atrium (RA) compliance; $C_{min,la}$ corresponds to a minimum values of the LA compliance; $C_{max,ra}$ corresponds to maximum values of RA compliance; $C_{max,la}$ corresponds to the maximum values of the LA compliance r; $C_i$; $i\in\{lv, rv\}$ is a systolic compliance across the LV and the RV; $d_{la}$ and d represents the delay in activation of the LA and the LV with respect to the RA; $u(t)$ and $u_v(t)$ define activation functions at a predefined time (t) in the LA, the RA, the LV and the RV, wherein the activation functions at the t is mathematically expressed as:

$$u(t) = \begin{cases} 0, & 0 \le t < T_a \\ 1 - \cos\left(2\pi \times n_{af} \times \frac{t-Ta}{T-T_a}\right), & T_a \le t < T \end{cases}$$

$$u_v(t) = \begin{cases} 0.5 - 0.5 \cos\left(\pi\frac{t}{T_1}\right), & 0 \le t < T_1 \\ 0.5 - 0.5 \cos\left(\pi\frac{t-T_1}{T_2-T_1}\right), & T_1 \le t < T_2 \\ 0, & T_2 \le t < T_{21} \end{cases}$$

where $T_a$ is an activation times across the RA; $T_1$, and $T_2$ are systolic and diastolic activation time instances of the cardiac cycle (T=60/HR); HR is the cardiac rhythm for the normal sinus rhythm; and $n_{af}$ is a decoupled factor of the LA with respect to the cardiac cycle, wherein under the normal sinus rhythm condition, $n_{af}=1$, such that the atrium and the ventricle pair operates synchronously;

constructing a plurality of blood inflow boundary conditions at a bilateral pulmonary vein inlets and a plurality of blood outflow boundary conditions at a mitral valve outlet, by using the plurality of cardiovascular parameters of the 0 D lumped cardiovascular hemodynamic model, generating a boundary conditions imposed 3D-CFD model;

calculating a mitral flow blood velocity, by performing a CFD analysis on the plurality of high density meshes of the boundary conditions imposed 3D-CFD model; and extracting a plurality of LA hemodynamic metrics of wall shear stress (WSS) that are possible indicators for progression of Atrial Fibrillation (AF), from the calculated mitral flow blood velocity, wherein the plurality of LA hemodynamic metrics comprises time average wall shear stress (TAWSS), oscillatory shear index (OSI) and endothelial cell activation potential (ECAP) are indicators for progression of the AF.

14. The one or more non-transitory machine-readable information storage mediums of claim 13, wherein the plurality of medical scan images comprises one of Computed Tomography (CT) scan images and Magnetic Resonance Imaging (MRI) scan images.

15. The one or more non-transitory machine-readable information storage mediums of claim 13, wherein creating the 3D-CFD model of the LA, from the received plurality of medical scan images comprises:

identifying, by a slice selection in an axial, a coronal and a sagittal plane, a plurality of substructures in the heart, from the plurality of medical scan images;

identifying a plurality of path lines that are connecting centres of the plurality of substructures;

performing segmentation, by using the plurality of the path lines, to generate a plurality of segmented sections, wherein cross-sectional areas of the plurality of substructures are segmented based on selection of a slice criterion corresponding to optimal substructures of the LA; and performing a loft operation, on to the plurality of segmented sections, generating the 3D-CFD model of the LA, wherein the loft operation performed on the plurality of segmented sections smoothens the 3D-CFD model of the LA for the CFD analysis, wherein the CFD analysis is governed by Navier-Stokes equations that represents combinations of continuity (mass balance) and momentum balance equations.

16. The one or more non-transitory machine-readable information storage mediums of claim 15, wherein the generated 3D-CFD model of the LA comprises four bilateral Pulmonary Veins (PVs) inlets, a LA chamber and outlet to a left ventricle (LV) via a mitral valve, wherein the four bilateral PVs comprises a Right Superior Pulmonary Vein (RSPV), a Right Inferior Pulmonary Vein (RIPV), a Left superior Pulmonary Vein (LSPV) and a Left inferior Pulmonary Vein (LIPV).

17. The one or more non-transitory machine-readable information storage mediums of claim 13, wherein the OD lumped cardiovascular hemodynamic model (i) regulates the systemic artery flow and, the pulmonary artery flow (ii) captures and replicates the LA dynamics and the LV dynamics, and volume dynamics during a cardiac cycle, wherein the LA dynamics and the LV dynamics replication of the OD lumped cardiovascular hemodynamic model at the LA and the LV, is expressed by a state space as:

$$P_{la} = \frac{1}{C_{la}(t)}\left[\frac{P_{la}-P_{pa}}{R_p} - U_{mi} \times \frac{P_{la}-P_{lv}}{R_{mi}} - C_{la}(t)P_{la}\right]$$

$$P_{la} = \frac{1}{C_{la}(t)}\left[\frac{P_{la}-P_{pa}}{R_p} - U_{mi} \times \frac{P_{la}-P_{lv}}{R_{mi}} - C_{la}(t)P_{la}\right]$$

where $P_{la}$, $P_{lv}$, $P_{sa}$, and $P_{pa}$ are pressure variables, capturing the LA dynamics and the LV dynamics, the systemic artery flow, the pulmonary artery flow; $R_{mi}$, $R_{ao}$ are valvular resistance across a mitral valve, and aortic valve; Ry is a vascular resistance; $C_{la}$, $C_{la}$ are the LA compliance and the LV compliance; $U_{mi}$, $U_{ao}$ are control inputs for opening and closing of heart valves and t is a function of time that varies with each cardiac cycle.

18. The one or more non-transitory machine-readable information storage mediums of claim 17, wherein the pressures variables that captured the LV dynamics, the systemic artery flow, the pulmonary artery flow extracts a plurality of LV hemodynamic metrics, wherein the plurality of LV hemodynamic metrics comprises an ejection fraction (EF), a mean arterial pressure (MAP) and a stroke volume, to analyze general cardiovascular health of the heart.

* * * * *